US008732546B2

(12) United States Patent
Fujita et al.

(10) Patent No.: US 8,732,546 B2
(45) Date of Patent: May 20, 2014

(54) RADIO RECEIVER WITH AN ERROR CORRECTION CODE DETECTOR AND WITH A CORRECTION UNIT

(75) Inventors: Manabu Fujita, Hino (JP); Toshiaki Shigemori, Hachioji (JP); Seiichiro Kimoto, Hachioji (JP); Ayako Nagase, Hachioji (JP); Akira Matsui, Hino (JP); Kazutaka Nakatsuchi, Hino (JP)

(73) Assignee: Olympus Corporation (JP)

( * ) Notice: Subject to any disclaimer, the term of this patent is extended or adjusted under 35 U.S.C. 154(b) by 385 days.

(21) Appl. No.: 13/165,513

(22) Filed: Jun. 21, 2011

(65) Prior Publication Data

US 2011/0252291 A1 Oct. 13, 2011

Related U.S. Application Data

(63) Continuation of application No. 11/576,512, filed as application No. PCT/JP2006/317008 on Aug. 29, 2006, now abandoned.

(30) Foreign Application Priority Data

Aug. 29, 2005 (JP) ................................. 2005-248011
Sep. 13, 2005 (JP) ................................. 2005-265704

(51) Int. Cl.
*H03M 13/00* (2006.01)

(52) U.S. Cl.
USPC ............................ 714/758; 714/775; 714/776

(58) Field of Classification Search
USPC ......................................... 714/758, 775, 776
See application file for complete search history.

(56) References Cited

U.S. PATENT DOCUMENTS 6,491,226 B1 12/2002 Nishioka 6,754,280 B2 * 6/2004 Nguyen ................... 375/240.28
(Continued)

FOREIGN PATENT DOCUMENTS

JP 4-205691 7/1992
JP 06-225273 8/1994
(Continued)

OTHER PUBLICATIONS

Office Action issued by the Japanese Patent Office on Aug. 9, 2011 in connection with corresponding Japanese Patent Application No. 2005-265704.

(Continued)

*Primary Examiner* — Esaw Abraham
(74) *Attorney, Agent, or Firm* — Ostrolenk Faber LLP

(57) ABSTRACT

A receiving apparatus for receiving a radio signal through an antenna. The radio signal is transmitted by a moving transmitting apparatus and has a frame configuration which includes at least a main information portion that includes information main part based on an image signal and an added portion that includes synchronization information and parameter information specific to the transmitting apparatus. The receiving apparatus includes a detecting unit that is configured to detect, from the received radio signal, an arrangement position of the parameter information in a frame configuration in which an error-correcting code is added immediately after the parameter information to be transmitted in a predetermined arrangement position of the frame configuration. A parameter information error correcting unit is configured to perform error correction on the parameter information with the error-correcting code that is added immediately after the detected arrangement position of the parameter information. An image processing unit is configured to perform image processing on the image signal of the main information portion using the corrected parameter information.

11 Claims, 11 Drawing Sheets

(56) References Cited

U.S. PATENT DOCUMENTS

| | | | |
|---|---|---|---|
| 6,975,752 B2 * | 12/2005 | Dixon et al. | 382/132 |
| 6,999,896 B2 * | 2/2006 | Takahashi | 702/181 |
| 7,198,343 B2 * | 4/2007 | Ebihara | 347/12 |
| 7,367,940 B2 | 5/2008 | Fujita et al. | |
| 7,472,317 B2 * | 12/2008 | Kikuchi et al. | 714/701 |
| 7,669,108 B2 * | 2/2010 | Kikuchi et al. | 714/775 |
| 7,810,733 B2 * | 10/2010 | Silverbrook et al. | 235/472.01 |
| 7,856,145 B2 * | 12/2010 | Ando et al. | 382/190 |
| 2002/0123672 A1 | 9/2002 | Christophersom et al. | |
| 2003/0011690 A1 | 1/2003 | Uryu | |
| 2005/0143649 A1 | 6/2005 | Minai et al. | |

FOREIGN PATENT DOCUMENTS

| | | |
|---|---|---|
| JP | 2001-216695 | 8/2001 |
| JP | 2002-330384 | 11/2002 |
| JP | 2003-19111 | 1/2003 |
| JP | 2002-247502 | 8/2003 |
| JP | 2004-171424 | 6/2004 |
| JP | 2004-524744 | 8/2004 |
| JP | 2005-143668 | 6/2005 |
| JP | 2005-157227 | 6/2005 |
| JP | 2005-192632 | 7/2005 |
| WO | WO 02/067591 | 8/2002 |
| WO | WO 02/067591 A2 | 8/2002 |

OTHER PUBLICATIONS

Translation of the Office Action issued by the Japanese Patent Office on Aug. 9, 2011 in connection with corresponding Japanese Patent Application No. 2005-265704.

Office Action issued by the Japanese Patent Office on Feb. 8, 2011 in connection with corresponding Japanese Patent Application No. 2005-248011.

Translation of the Office Action issued by the Japanese Patent Office on Feb. 8, 2011 in connection with corresponding Japanese Patent Application No. 2005-248011.

Search Report issued by European Patent Office in connection with corresponding application No. EP 06 796 985.7 on Oct. 6, 2010.

Chinese Office Action mailed Aug. 21, 2009 in corresponding Chinese Patent Application No. 200680031621.X (in Chinese language).

PCT/JP2006/317008 International Search Report dated Oct. 10, 2006.

Final Office Action for corresponding Japanese Application No. 2005-248011 issued on Jun. 7, 2011.

* cited by examiner

RADIO RECEIVER WITH AN ERROR CORRECTION CODE DETECTOR AND WITH A CORRECTION UNIT

CROSS-REFERENCE TO RELATED APPLICATIONS

This application is a continuation of abandoned prior application Ser. No. 11/576,512, filed Apr. 2, 2007 by Manabu FUJITA, et al. entitled RECEIVING APPARATUS, which is a continuation of PCT international application Ser. No. PCT/JP2006/317008, filed Aug. 29, 2006, and which claims the benefit of priority from JP No. 2005-248011, filed Aug. 29, 2005, and JP No. 2005-265704, filed Sep. 13, 2005, all of which are incorporated herein by reference.

TECHNICAL FIELD

The present invention relates to a receiving apparatus that receives a radio signal transmitted from a body-insertable apparatus such as a capsule endoscope to be introduced into a subject, and records the radio signal on a portable recording medium detachably attached thereto.

BACKGROUND ART

Recently, in the field of endoscope, a capsule endoscope equipped with an imaging function and a radio communication function has appeared. This capsule endoscope has a configuration of moving in the internal organs (body cavity) such as esophagus, stomach, and small intestine with peristalsis during an observation period after it is swallowed from a mouth of an examinee as a subject of observation (examination) until it is naturally discharged from a living body (human body) of the examinee, and sequentially taking pictures at a predetermined imaging rate by using the imaging function.

During this observation period while the endoscope is moving in the internal organs, image data acquired in the body cavity by the capsule endoscope is sequentially transmitted to the outside of the examinee by the radio communication function such as radio communications, and stored in a memory provided in an external receiving device. If the examinee carries the receiving device having the radio communication function and the memory function, the examinee swallows the capsule endoscope and then can freely move without any inconvenience even during the observation period until the endoscope is discharged. After the observation, a doctor or a nurse can perform diagnosis by displaying images of the body cavity on a display unit, such as a display, based on the image data stored in the memory in the receiving device (see Patent Document 1).

Patent Document 1: Japanese Patent Application Laid-open No. 2003-19111

DISCLOSURE OF INVENTION

Problem to be Solved by the Invention

As a memory provided in the receiver, for example, it has been proposed to use a portable recording medium such as a CompactFlash® Memory, which is detachable relative to a receiver and a display device such as a workstation, and has a structure capable of outputting or recording information at the time of being set in both the receiver and the workstation. In other words, while the capsule endoscope is moving in a body cavity of the subject, the portable recording medium is set in the receiver attached to the subject to record data transmitted from the capsule endoscope, and after the capsule endoscope is discharged from the subject, the portable recording medium is taken out from the receiver and set in the display device, so that the display device reads the data recorded on the portable recording medium. Since transfer of data between the receiver and the display device is performed by the portable recording medium, the subject can freely moves during taking pictures of the body cavity, which also contributes to reduction of a transfer period of data between the receiver and the display device.

However, since the portable recording medium is detachable to the receiver, even while the data of the body cavity imaged by the capsule endoscope is being received and recorded, if a user (such as a doctor, a nurse, or a patient) wishes to eject the portable recording medium from the receiver, the portable recording medium can be ejected. If the portable recording medium is erroneously ejected from the receiver during receiving and recording data (during examination), the receiver cannot record and store the imaged data of the body cavity transmitted from the capsule endoscope and received, and hence the sequentially acquired valuable imaged data of the body cavity for the examination is lost. In other words, since the examination by the capsule endoscope extends over a long time, for example, about eight hours, the examination cannot be redone. Hence, if the imaged data of the body cavity is lost, such an examination becomes meaningless. Furthermore, if the portable recording medium is ejected during a recording operation, the recording medium itself is damaged, and the imaged data of the body cavity already recorded may not be used. However, if a lock mechanism against ejection of the recording medium is strengthened, not only the structure becomes complicated, but also unloading operability of the recording medium deteriorates. Conventionally, an effective measure against such a state has not been taken.

The present invention has been achieved to solve the above problems, and it is an object of the present invention to provide a receiving apparatus that can prevent beforehand the portable recording medium from being erroneously ejected, and can prevent the imaged data of the body cavity from being lost and the portable recording medium from being damaged.

Means for Solving Problem

To solve the above problems and achieve the object, a receiving apparatus according to the present invention receives a radio signal transmitted from a body-insertable apparatus introduced into a subject, and records the radio signal on a portable recording medium detachably attached thereto, and includes an in-operation detector that detects that a recording operation is in progress, an ejection operation detector that detects an ejection operation of the portable recording medium, a warning unit that gives a warning to a user, and a control unit that operates the warning unit before the portable recording medium is ejected, when the ejection operation of the portable recording medium is detected during the recording operation.

In the receiving apparatus according to the present invention, the portable recording medium is detachably attached by a plurality of operations or actions, and the ejection operation detector detects the ejection operation of the portable recording medium, at the time of starting the first one of the plurality of operations or actions.

In the receiving apparatus according to the present invention, the warning unit generates a warning by a warning display on a display unit.

In the receiving apparatus according to the present invention, the warning unit generates a warning by lighting-on or blinking of a light emission element.

In the receiving apparatus according to the present invention, the light emission element is provided near an ejector of the portable recording medium.

In the receiving apparatus according to the present invention, the warning unit generates a warning by a warning sound.

Effect of the Invention

According to the receiving apparatus of the present invention, when the ejection operation of the portable recording medium is detected, the warning unit is operated before the portable recording medium is ejected to give a warning to the user so that the ejection operation is not performed. Accordingly, it can be prevented beforehand that the portable recording medium is erroneously ejected during the recording operation, and hence it can be prevented that the imaged data of the body cavity is lost and the portable recording medium is damaged.

EXPLANATIONS OF LETTERS OR NUMERALS

1 Subject
2 Receiving apparatus
3 Capsule endoscope
5 Portable recording medium
23 LED
24 Display unit
25 Speaker

BEST MODE(S) FOR CARRYING OUT THE INVENTION

Exemplary embodiments of a receiving apparatus according to the present invention will be explained below in detail with reference to the accompanying drawings. Note that the present invention is not limited to the embodiments, and the embodiments can be variously modified within the range of the scope of the present invention.

First Embodiment

Figure 1:
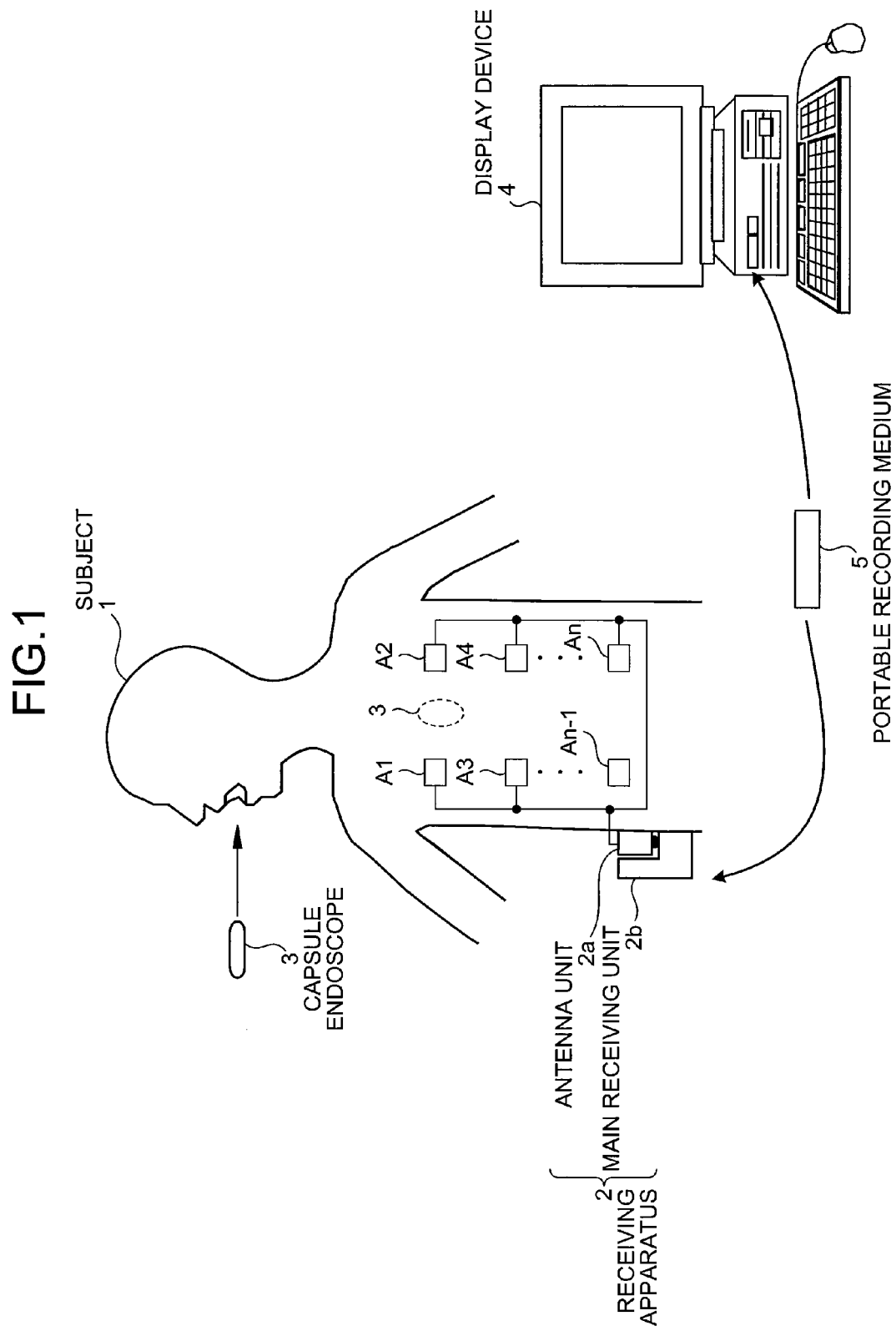
FIG. 1 is a schematic diagram of an overall configuration diagram of a wireless in-vivo information acquiring system according to a first embodiment of the present invention.

FIG. 1 is a schematic diagram of an overall configuration diagram of a wireless in-vivo information acquiring system according to a first embodiment of the present invention. The wireless in-vivo information acquiring system uses a capsule endoscope as one example of the body-insertable apparatus, which is a transmitting unit. In FIG. 1, the wireless in-vivo information acquiring system includes a receiving apparatus 2 having a radio receiving function, and a capsule endoscope 3 introduced into a subject 1 to take pictures of body cavity images and transmits data such as an image signal to the receiving apparatus 2. The wireless in-vivo information acquiring system also includes a display device 4 that displays the body cavity image based on the image signal received by the receiving apparatus 2, and a portable recording medium 5 for transferring data between the receiving apparatus 2 and the display device 4. The receiving apparatus 2 includes an antenna unit 2a including a plurality of receiving antennas A1 to An attached to the body surface of the subject 1, and a main receiving unit 2b as a main receiving apparatus that performs processing of radio signals received via the receiving antennas A1 to An, and these units are detachably connected with each other via a connector or the like. The receiving antennas A1 to An can be equipped on a receiving jacket wearable by the subject, and the subject 1 can carry the receiving antennas A1 to An by wearing the receiving jacket. In this case, the receiving antennas A1 to An can be detachable to the jacket.

The display device 4 displays the body cavity images and the like taken by the capsule endoscope 3, and has a configuration of a workstation or the like that displays images based on data acquired by the portable recording medium 5. Specifically, the display device 4 can have a configuration such that images are directly displayed by a CRT display, a liquid crystal display, or the like, or a configuration such that images are output to other media, like a printer.

As the portable recording medium 5, a CompactFlash® Memory or the like is used, which is detachable relative to the main receiving unit 2b and the display device 4, and has a structure capable of outputting or recording information at the time of being set in both the main receiving unit 2b and the display device 4. In the first embodiment, the portable recording medium 5 is set in the display device 4 of a workstation, for example, before examination, to store identification information such as an examination ID, and immediately before the examination, is set in the main receiving unit 2b and the identification information is read by the main receiving unit 2b and registered in the main receiving unit 2b. While the capsule endoscope 3 is moving in the body cavity of the subject 1, the portable recording medium 5 is set in the main receiving unit 2b attached to the subject 1, to record data transmitted from the capsule endoscope 3. After the capsule endoscope 3 is discharged from the subject 1, that is, after imaging of the inside of the subject 1 has finished, the portable recording medium 5 is taken out from the main receiving unit 2b and set in the display device 4, so that the display device 4 reads the data recorded on the portable recording medium 5. For example, since transfer of data between the main receiving unit 2b and the display device 4 is performed by the portable recording medium 5, the subject 1 can freely move during taking pictures of the body cavity, which also contributes to reduction of a transfer period of data between the main receiving unit 2b and the display device 4.

Figure 2:
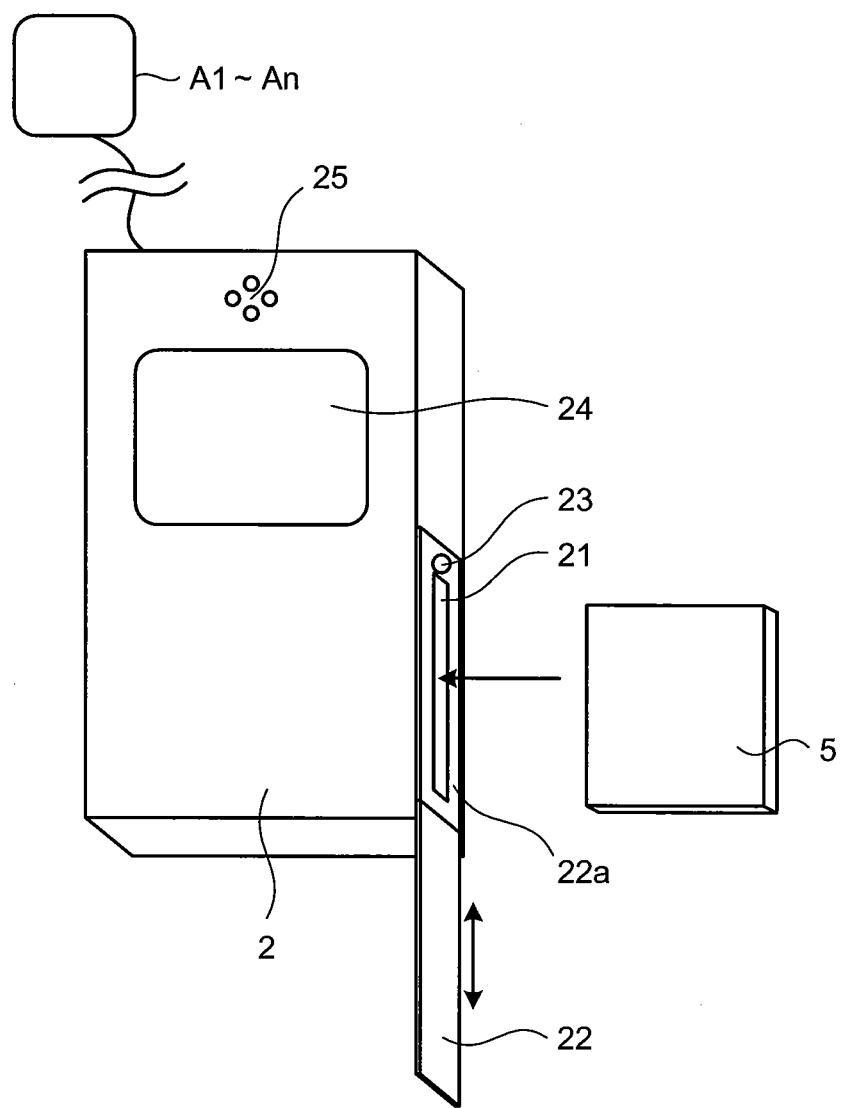
FIG. 2 is a schematic diagram of an outline of appearance of a receiving apparatus.
Figure 3:
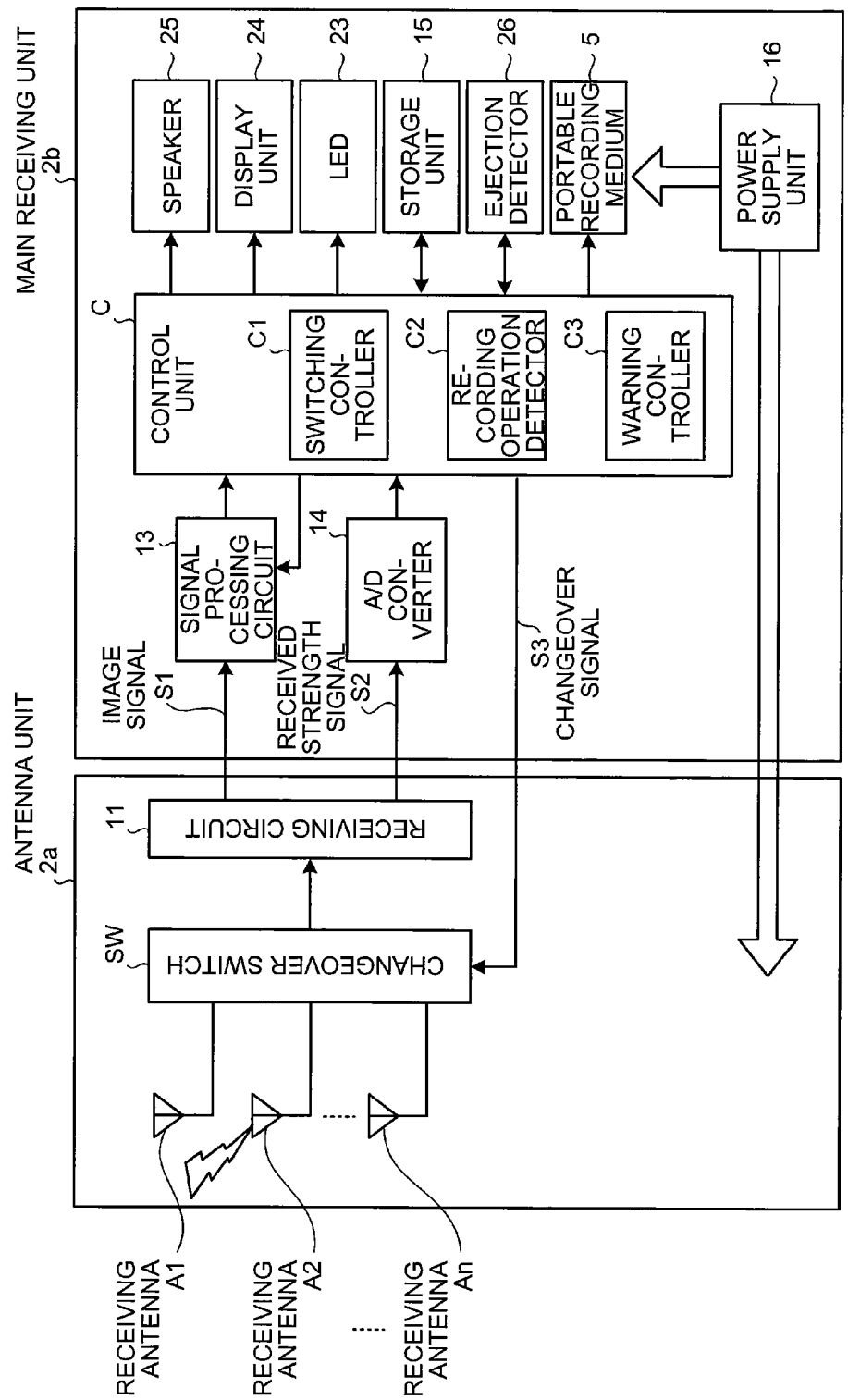
FIG. 3 is a schematic block diagram of a configuration example of the receiving apparatus.

A configuration of the receiving apparatus is explained by using a schematic diagram in FIG. 2 and a block diagram in FIG. 3. The receiving apparatus 2 has a function for receiving image data of the body cavity wirelessly transmitted from the capsule endoscope 3. As shown in FIGS. 2 and 3, the receiving apparatus 2 has a shape detachable and portable by the subject 1, and includes the antenna unit 2a and the main receiving unit 2b detachably connected to the antenna unit 2a. The antenna unit 2a receives the radio signal transmitted from the capsule endoscope 3 via the receiving antennas A1 to An, demodulates the radio signal to an image signal and outputs the image signal, and the main receiving unit 2b performs signal processing of the image signal.

As shown in FIG. 2, a card insertion port 21 for inserting the portable recording medium 5 is formed in a slit shape on the side of the main receiving unit 2b, and a card cover 22 that closes the card insertion port 21 is provided slidably by a guide member 22a. Therefore, in the first embodiment, the portable recording medium 5 is set in the main receiving unit 2b by sliding the card cover 22 to open the card insertion port 21 and inserting the portable recording medium 5 from the card insertion port 21 to plug in an internal connector. On the other hand, at the time of taking out the portable recording medium 5, the portable recording medium 5 cannot be taken out only by one action, and requires two actions, that is, an operation (action) for sliding and opening the card cover 22, and an operation (action) for pulling the portable recording medium 5 exposed due to the release of the card cover 22 out from the card insertion port 21 (or pushing the portable recording medium 5 temporarily).

In the main receiving unit 2b, an LED 23 is provided near the card insertion port 21 as a light emission element for the warning unit. A display unit 24 formed of a liquid crystal display, for example, an LCD is provided on the front of the main receiving unit 2b, for example, for displaying registered identification information such as the examination ID. A speaker 25 for properly outputting information by speech is provided on the upper front of the main receiving unit 2b.

The antenna unit 2a includes, as shown in FIG. 3, a changeover switch SW that selectively switches connection any one of the receiving antennas A1 to An, and a receiving circuit 11 connected to a subsequent stage of the changeover switch SW for amplifying the radio signal from the receiving antennas A1 to An switched by the changeover switch SW, and demodulating the radio signal to the image signal as transmission information.

The main receiving unit 2b receives the image signal demodulated by the antenna unit 2a to perform signal processing. The main receiving unit 2b includes a signal processing circuit 13 connected at a subsequent stage of the receiving circuit 11, an A/D converter 14, a storage unit 15 that stores various pieces of information, the portable recording medium 5, the LED 23, the display unit 24, the speaker 25, an ejection detector 26, a control unit C that controls these respective components, and a power supply unit 16 that supplies power to the main receiving unit 2b and the antenna unit 2a.

The ejection detector 26 is formed of a mechanical switch or the like to detect the ejection operation of the portable recording medium 5. More specifically, it is configured so as to detect the ejection operation of the portable recording medium 5, during the ejection operation requiring two actions, and at the time of starting an operation for sliding and opening the card cover 22, which is the first operation.

The signal processing circuit 13 performs signal processing such as serial/parallel conversion, pixel interpolation processing, and image compression processing, relative to the image signal data demodulated by the receiving circuit 11 such as the antenna unit 2a. The control unit C includes a switching controller C1 that controls changeover of the antenna, a recording operation detector C2 as an operation detector that detects that the recording operation is in progress, and a warning controller C3 as a control unit that controls whether a warning by lighting or blinking, which indicates that the ejection operation should not be performed, is to be given to the user through the LED 23.

The receiving circuit 11 amplifies the radio signal output from the changeover switch SW, and outputs a demodulated image signal S1 to the signal processing circuit 13, and a received strength signal S2 indicating the signal strength of the amplified radio signal to the A/D converter 14. The image data processed by the signal processing circuit 13 is stored in the portable recording medium 5 by the control unit C, and the image is displayed on the display unit 24 according to need. The received strength signal S2 converted to a digital signal by the A/D converter 14 is fetched by the control unit C. The switching controller C1 selects a receiving antenna having received the data with the largest signal strength as a receiving antenna for acquiring the image data, based on the received strength signal S2 obtained by sequentially switching the receiving antennas A1 to An, and outputs a changeover signal S3 instructing the changeover to the antenna to the changeover switch SW. Further, the control unit C stores the signal strength received by the respective receiving antennas in the portable recording medium 5 together with the image data, in correspondence with the selected receiving antenna. The stored signal strength of the respective receiving antennas becomes the information for calculating the position of the capsule endoscope 3 in the subject at the time of receiving the image data.

The recording operation detector C2 detects that a recording operation relative to the mounted portable recording medium 5 is in progress (is under examination). For example, in a stage where after a power supply of the main receiving unit 2b is turned on, a synchronization signal for triggering is not detected from the radio signal transmitted from the capsule endoscope 3, it is determined to be before starting the recording operation (before starting examination), and once the synchronization signal is detected, it is determined to be after starting the recording operation. Alternatively, since the format of the portable recording medium 5 is initialized before starting the examination, by looking at the write state to the portable recording medium 5, it can be determined to be before starting the recording operation in a stage where the body cavity image data has not yet been written on the portable recording medium 5. Further, one examination using the capsule endoscope 3 finishes after a certain period of time has passed since the start of recording, for example, after about eight hours, and the capsule endoscope 3 is discharged outside of the body cavity. Therefore, an elapsed time since the start of a recording operation is monitored, and after the certain period of time has passed, it can be determined that the recording operation has finished.

The warning controller C3 gives a warning to the user by lighting-on or blinking of the LED 23 before the portable recording medium 5 is ejected from the card insertion port 21, when the ejection operation of the portable recording medium 5 is detected by the ejection detector 26 during the recording operation, to control the operation of the LED 23.

Figure 4:
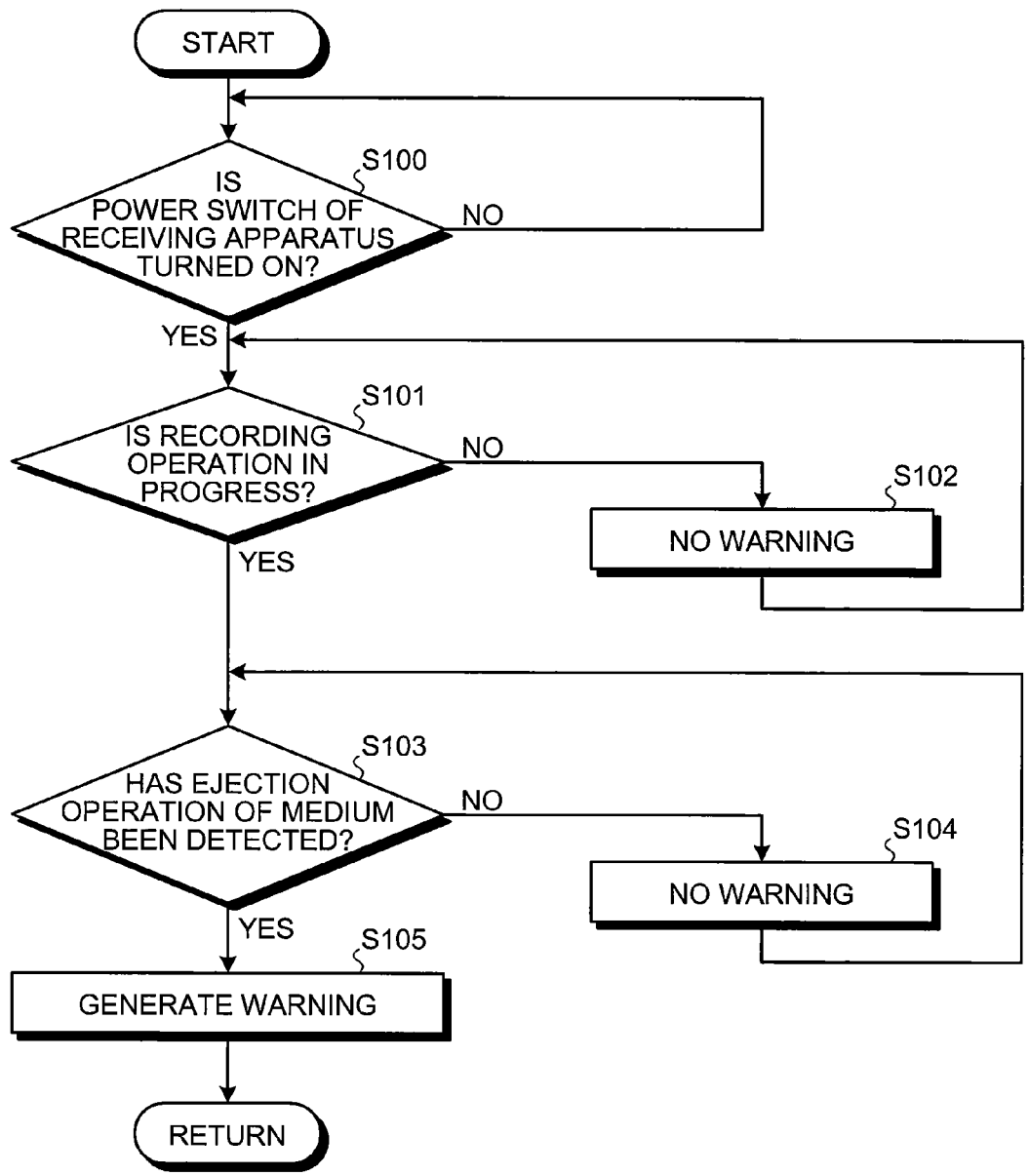
FIG. 4 is a schematic flowchart in a warning control example with respect to a medium ejection operation.

A warning control example with respect to a medium ejection operation executed by the control unit C in the first embodiment is explained, with reference to a schematic flowchart shown in FIG. 4. This process is executed in such a state that the power switch of the receiving apparatus 2 (the main receiving unit 2b) is turned on (step S100: Yes). In such a state, it is determined whether the recording operation is in progress by the detection operation of the recording operation detector C2 (step S101). If the recording operation is in progress (step S101: No), the portable recording medium 5 can be freely ejected, and a warning to the user is not required. Therefore, warning by the LED 23 is not performed (step S102).

If the recording operation is in progress (step S101: Yes), it is determined whether the ejection operation of the portable recording medium 5 has been detected by referring to the detection result by the ejection detector 26 (step S103). When the ejection operation of the portable recording medium 5 has not been detected (step S103: No), it is a normal state, and hence a warning to the user is not required. Therefore, warning by the LED 23 is not performed (step S104).

On the other hand, during the recording operation (step S101: Yes), when the ejection operation of the portable recording medium 5 has been detected (step S103: Yes), it is an abnormal state, and hence the LED 23 is controlled so as to be lighted on or blinked, thereby giving a warning to the user so as not to perform the ejection operation of the portable recording medium 5 (step S105).

By giving such a warning, it can be prevented beforehand that the portable recording medium 5 is erroneously ejected during the recording operation, and hence the body cavity image data can be prevented from being lost and the portable recording medium can be prevented from being damaged. Particularly in the present embodiment, two actions are required for ejecting the portable recording medium 5, and the ejection operation is detected at the time of starting the opening operation of the card cover 22, which is the first operation, and at this point in time, a warning so as not to perform the ejection operation is generated before the portable recording medium 5 is pulled out from the connector. Accordingly, the portable recording medium 5 can be prevented beforehand from being detached from the connector during the recording operation. In addition, since the warning is generated by the LED 23 provided near the card insertion port 21, from which the portable recording medium 5 is ejected, a warning so as not to perform ejection can be given to the user effectively.

While in the first embodiment, a warning is generated by lighting-on or blinking of the LED 23, a warning message, such as "Recording in progress. Do not eject the card.", can be displayed on the display unit 24. Alternatively, a warning sound for stopping the user to eject the card can be issued via the speaker 25.

In the first embodiment, further, ejection of the portable recording medium 5 requires two actions (operations or actions), that is, an operation for opening the card cover 22, and an operation for pulling out the portable recording medium 5. However, the actions are not limited thereto, and for example, two actions can include the opening operation of the card cover and a pressing operation of an eject bar, or two actions can include a lock release operation and the operation for pulling out the portable recording medium 5.

Second Embodiment

The wireless in-vivo information acquiring system corresponds to a transmitting/receiving system, and the capsule endoscope is used as one example of a transmission apparatus (body-insertable apparatus).

Figure 5:
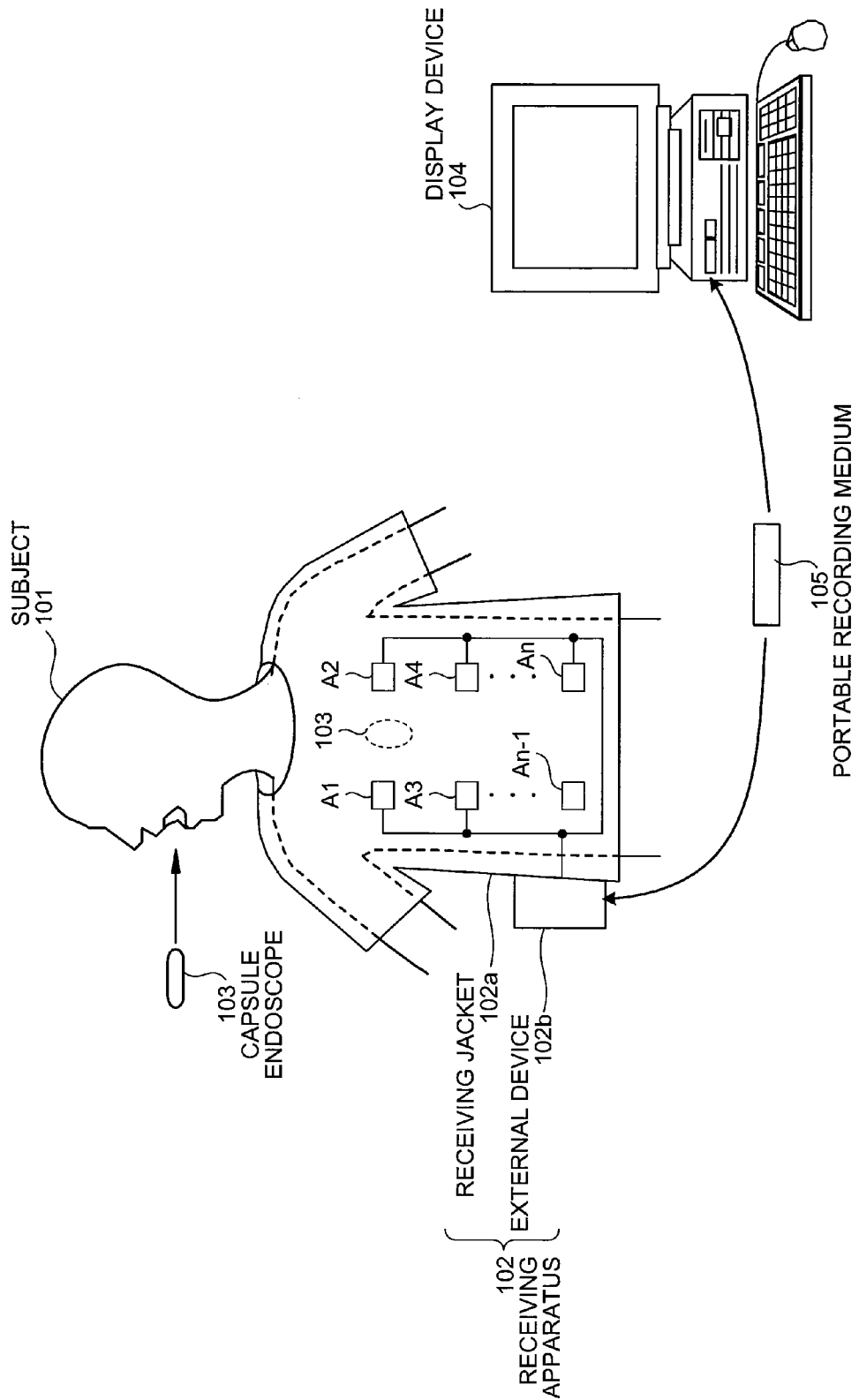
FIG. 5 is a schematic diagram of an overall configuration of a wireless in-vivo information acquiring system according to a second embodiment.

FIG. 5 is a schematic diagram of an overall configuration of the wireless in-vivo information acquiring system. As shown in FIG. 5, the wireless in-vivo information acquiring system includes a receiving apparatus 102 having a radio receiving function, and a capsule endoscope (body-insertable apparatus) 103 introduced into the body of a subject 101 to take pictures of the body cavity and perform wireless data transmission of image signals and the like with respect to the receiving apparatus 102. The in-vivo information acquiring system further includes a display device 104 that displays the body cavity image based on the image signal received by the receiving apparatus 102, and a portable recording medium 105 that performs data transfer between the receiving apparatus 102 and the display device 104. The receiving apparatus 102 includes a receiving jacket 102a worn by the subject 101 and an external device 102b that performs processing of the radio signal received via the receiving jacket 102a.

The display device 104 displays the body cavity image taken by the capsule endoscope 103, and has a configuration of a workstation or the like that displays images based on the data acquired by the portable recording medium 105. Specifically, the display device 104 can have a configuration of directly displaying images by a CRT display, a liquid crystal display, or the like, or a configuration of outputting images to other media like a printer.

The portable recording medium 105 has a configuration detachable to the external device 102b and the display device 104, and capable of outputting or recording information when the portable recording medium 105 is set in the external device 102b and the display device 104. Specifically, the portable recording medium 105 is set in the external device 102b to record data transmitted from the capsule endoscope 103, when the capsule endoscope 103 is moving in the body cavity. When the capsule endoscope 103 is discharged from the subject 101, that is, when imaging of the inside of the subject 101 has finished, the portable recording medium 105 is taken out from the external device 102b and set in the display device 104, and the recorded data is read by the display device 104. By performing data transfer between the external device 102b and the display device 104 by the portable recording medium 105 such as a CompactFlash® Memory or the like, the subject 101 can freely move during imaging of the body cavity, than in a case when the external device 102b and the display device 104 are connected with each other by wire, which further contributes to reduction of the data transfer time between the external device 102b and the display device 104. Here, the portable recording medium 105 is used for the data transfer between the external device 102b and the display device 104. However, the present invention is not limited thereto, and another built-in recording device can be used for the external device 102b, and the built-in recording device can be connected to the display device 104 by wire or wireless connection for the data transfer.

Figure 6:
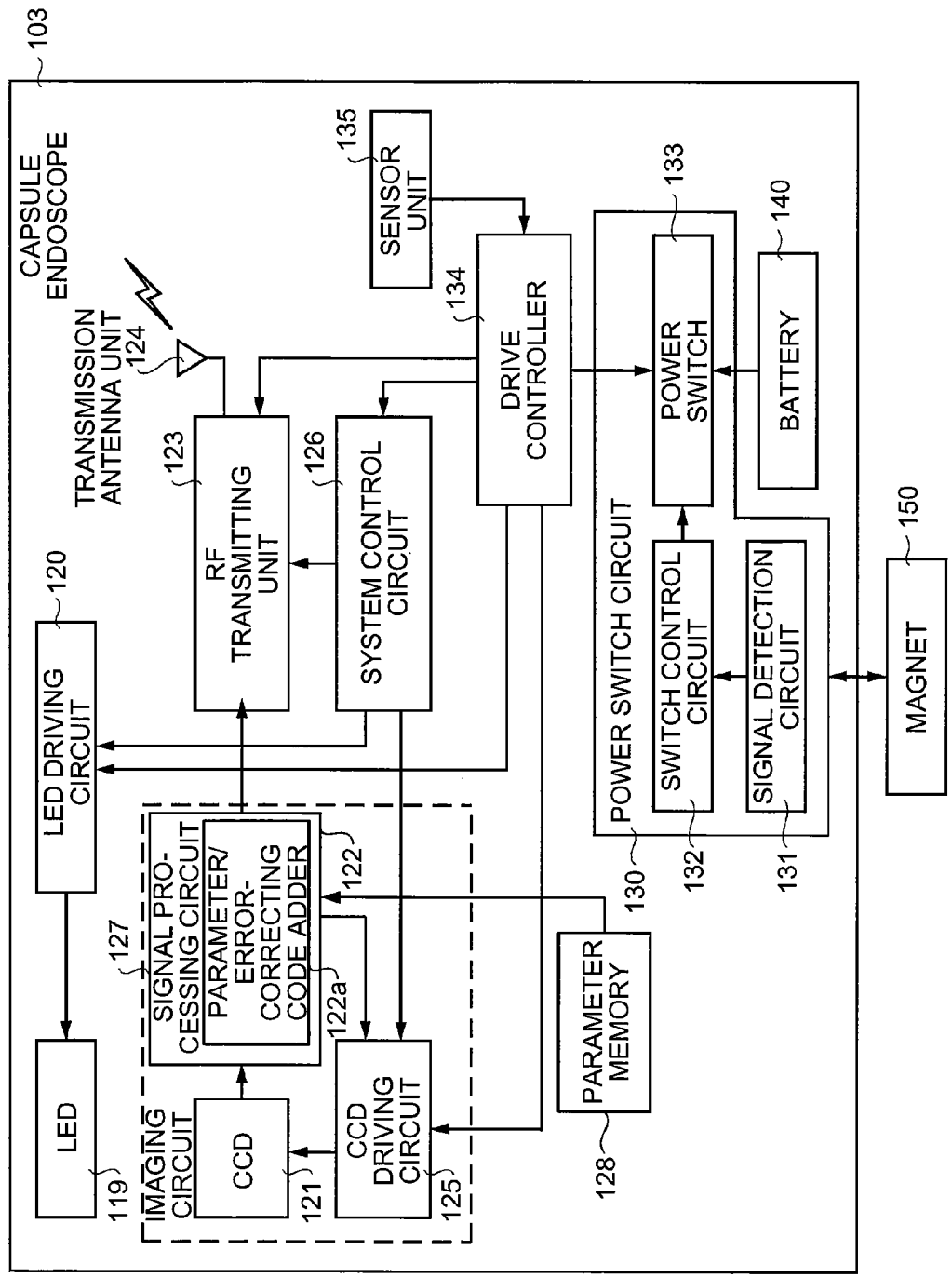
FIG. 6 is a block diagram schematically showing a configuration of a capsule endoscope according to the second embodiment.

Here, the capsule endoscope 103 is explained. FIG. 6 is a block diagram schematically showing a configuration of the capsule endoscope 103. The capsule endoscope 103 includes an LED 119 for irradiating an imaging area at the time of imaging the inside of the subject 101, an LED driving circuit 120 that controls driving state of the LED 119, a CCD 121 as an imaging device that images the area irradiated by the LED 119, and a signal processing circuit 122 that processes the image signal output from the CCD 121 to imaging information in a desired shape. The capsule endoscope 103 further includes a CCD driving circuit 125 that controls driving state of the CCD 121, an RF transmitting unit 123 that generates an RF signal by modulating the image data imaged by the CCD 121 and processed by the signal processing circuit 122, a transmission antenna unit 124 that transmits an RF signal output from the RF transmitting unit 123, and a system control circuit 126 that controls an operation of the LED driving circuit 120, the CCD driving circuit 125, and the RF transmitting unit 123. The CCD 121, the signal processing circuit 122, and the CCD driving circuit 125 are collectively referred to as an imaging circuit 127.

By having these mechanisms, the capsule endoscope 103 acquires image information of a region to be examined irradiated by the LED 119 by the CCD 121, while the capsule endoscope 103 is introduced in the subject 101. The acquired image information is subjected to signal processing and converted to an image signal by the signal processing circuit 122, and the image signal is converted to an RF signal in the RF transmitting unit 123, and transmitted to the outside via the transmission antenna unit 124.

The signal processing circuit 122 includes a parameter/error-correcting code adder 122a. The parameter/error-correcting code adder 122a adds white balance factor data "WB" as parameter information specific to the capsule endoscope 103 stored beforehand in a parameter memory 128; ID information "ID" specific to the capsule; and Reed-Solomon codes "RS 1" and "RS2" as error-correcting code data respectively for the white balance factor data "WB" and the ID information "ID" specific to the capsule, so that these data are transmitted at a predetermined arrangement position specified beforehand so as to be synchronized with a vertical synchronization signal and a horizontal synchronization signal of the image signal in one frame.

In other words, in the second embodiment, the capsule endoscope 103 transmits a radio signal having a frame configuration including at least main information that includes information main part based on the image signal acquired by imaging, and an added portion that includes synchronization information, the white balance factor data "WB" as the parameter information specific to the capsule endoscope 103, and the ID information "ID" specific to the capsule. The Reed-Solomon codes "RS1" and "RS2" are added immediately after the white balance factor data "WB" and the ID information "ID" specific to the capsule.

Figure 9:
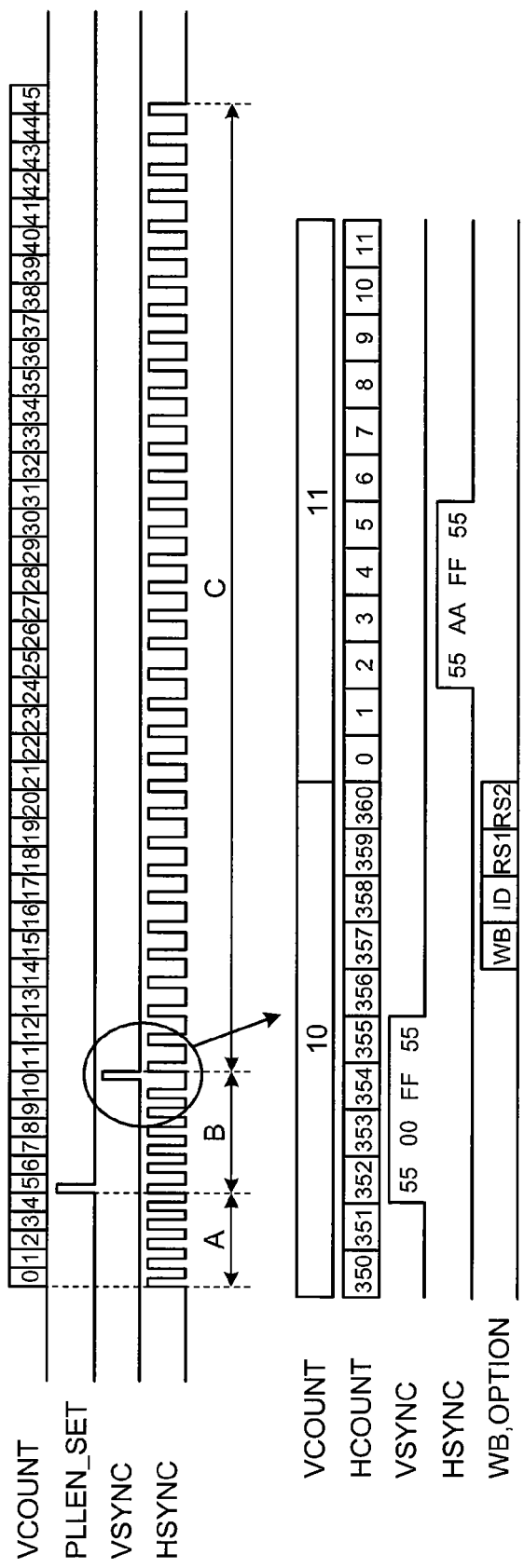
FIG. 9 is a timing chart of a receiving operation of the receiving apparatus according to the second embodiment.

With reference to FIG. 9 indicating a timing chart of the receiving operation of the receiving apparatus 102, a 16-bit code of "55 00 FF 55" is used as a code indicating the vertical synchronization signal VSYNC (VD), and the 16-bit code is allocated to particular line positions specified by "352", "353", "354", and "355" as count values HCOUNT of the horizontal synchronization signal in a phase having a count value VCOUNT of "10" since start of the operation, and transmitted. Further, a 16-bit code of "55 AA FF 55" is used as a code indicating the horizontal synchronization signal HSYNC (HV), and the 16-bit code is allocated to particular line positions specified by "2", "3", "4", and "5" as count values HCOUNT of the horizontal synchronization signal in a phase having a count value VCOUNT of "11" since start of the operation, and transmitted. The white balance factor data "WB", the ID information "ID" specific to the capsule, and the Reed-Solomon codes "RS1" and "RS2" are data, for example, of 1 byte respectively, and in total, 4-byte data, and are set so that these data are respectively allocated to the particular line positions specified by "357", "358", "359", and "360" as count values HCOUNT of the horizontal synchronization signal in the phase having a count value VCOUNT of "10", between the code indicating the vertical synchronization signal VSYNC (VD) and the code indicating the horizontal synchronization signal HSYNC (HV), and transmitted. In FIG. 9, a period A indicates a waiting time until a receiving circuit 111 of the receiving apparatus 102 is turned on and stabilized, a period B indicates a waiting time until an PLL circuit in a clock recovery 161 is turned on and locked, and a period C indicates a receiving period of the image signal.

The white balance factor data "WB" is data for performing white balance processing with respect to imaged data by the CCD 121, and is obtained as a white balance factor specific to the CCD 121 beforehand by a test in a manufacturing process of the respective capsule endoscopes 103. Specifically, a white chart as a reference is imaged by the CCD 121, and a correction factor (white balance factor) is calculated so that outputs of red (R) and blue (B) become specified values, using green (G) as a reference, and stored in the parameter memory 128.

The specific parameter information is not limited to the data of the white balance factor, and for example, can be data indicating an address of a pixel defect of the CCD 121, and can be used for correcting the pixel defect present at the address based on pixel data corresponding to a peripheral address of the address of the pixel defect. Further, an offset value of a photoelectric transfer characteristic, which is a value specific to each CMOS sensor, for example, when the CMOS sensor is used as the imaging device instead of the CCD, can be stored beforehand in the parameter memory 128 as a parameter for the signal processing specific to each device.

The ID information "ID" specific to the capsule is identification number data added beforehand for each capsule endoscope 103 to determine the capsule endoscope 103 individually, and stored in the parameter memory 128 beforehand.

The Reed-Solomon codes "RS1" and "RS2" are codes calculated as error-correcting codes relative to the already calculated and set white balance factor data "WB" and ID information "ID" specific to the capsule, and stored in the parameter memory 128 beforehand. The error-correcting codes need not always be the Reed-Solomon codes, and other codes, for example, Hamming codes can be used.

The capsule endoscope 103 includes a sensor unit 135 that detects predetermined signals such as magnetic, optical, or radio signals, and a drive controller 134 that controls drive of the system control circuit 126 that performs overall control of processing of the LED driving circuit 120, the CCD driving circuit 125, the RF transmitting unit 123, and respective units, based on a value detected by the sensor unit 135. The sensor unit 135 is achieved by, for example, a pH sensor, and detects whether the capsule endoscope 103 has reached a predetermined position in the subject, and the drive controller 134 controls the drive of respective units based on the result. Accordingly, power consumption can be reduced.

The drive controller 134 is supplied with power from a battery 140 as an energy source via a power switch 133 in a power switch circuit 130. The battery 140 is achieved, for example, by a button battery such as silver oxide. The power switch 133 is a main power switch of the capsule endoscope 103. The power switch circuit 130 has a signal detection circuit 131 and a switch control circuit 132. The signal detection circuit 131 that detects a signal from the outside of the capsule endoscope 103 is achieved by a reed switch, and is turned on or off when a magnet 150 approaches to or is separated from the reed switch. That is, the switch control circuit 132 that performs an on or off operation based on whether a magnetic force acts on the reed switch controls such that on/off of the power switch 133 is toggled based on the control signal from the signal detection circuit 131, that is, the on/off signal. The on/off of the power switch 133 by the magnet 150 is performed before the capsule endoscope 103 is introduced into the subject 101, to check the operation of the capsule endoscope 103.

Figure 7:
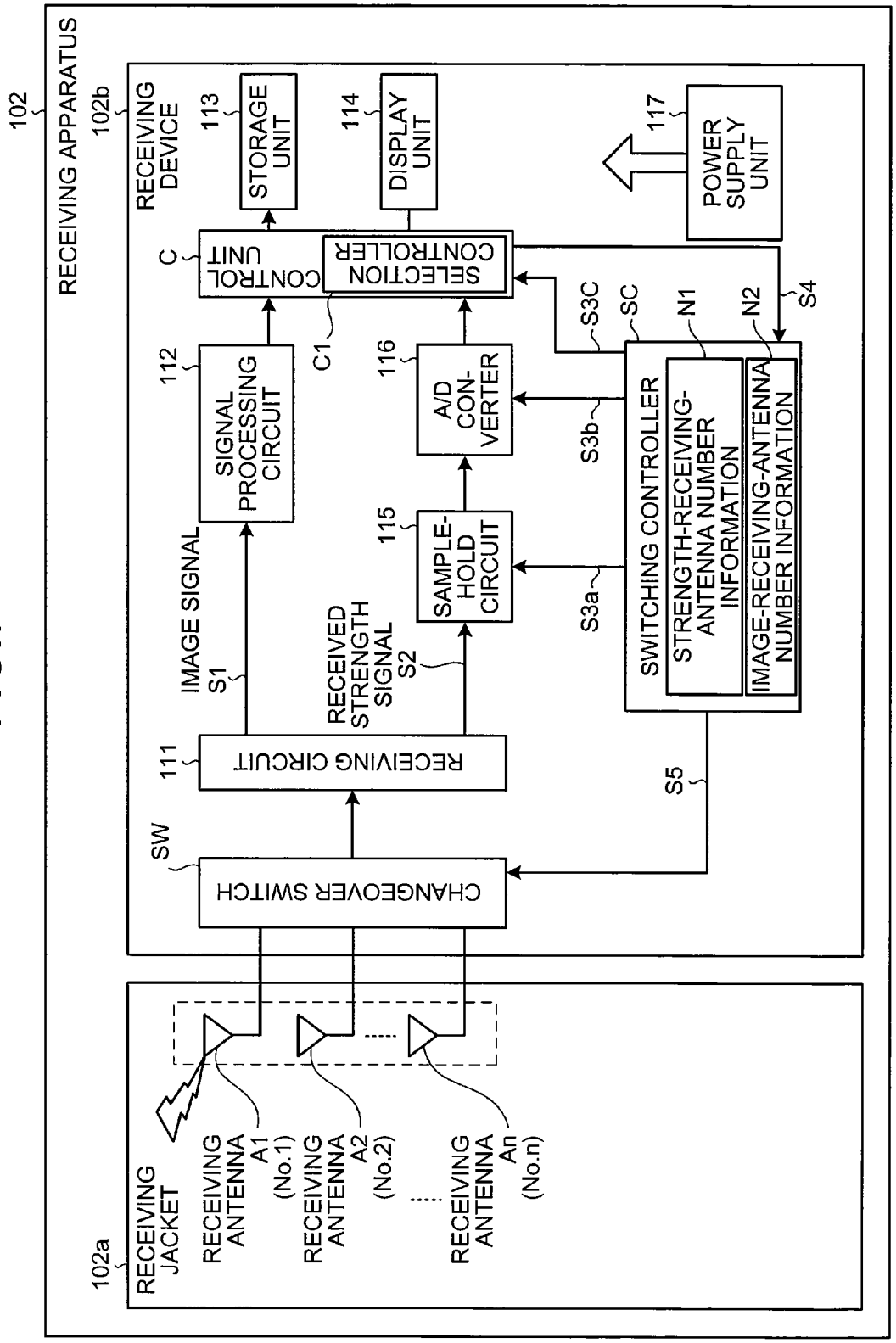
FIG. 7 is a block diagram schematically showing a configuration of a receiving apparatus according to the second embodiment.

The receiving apparatus 102 is explained with reference to FIG. 7. The receiving apparatus 102 has a function for receiving body cavity image data wirelessly transmitted from the capsule endoscope 103. FIG. 7 is a block diagram schematically showing a configuration of the receiving apparatus. As shown in FIG. 7, the receiving apparatus 102 has a shape wearable by the subject 101, and includes the receiving jacket 102a having receiving antennas A1 to An, and the external device 102b that processes the received radio signals. Each of the receiving antennas A1 to An can be equipped on the receiving jacket 102a so as to be directly adhered on the body surface of the subject, and can be detachable from the receiving jacket 102a.

The external device 102b has a function for processing the radio signals transmitted from the capsule endoscope 103. Specifically, the external device 102b includes a changeover switch SW that switches connection of the receiving antennas A1 to An, the receiving circuit 111 connected to a subsequent stage of the changeover switch SW for amplifying and demodulating the radio signal from the receiving antennas A1 to An switched by the changeover switch SW. A signal processing circuit 112 and a sample-hold circuit 115 are connected to a subsequent stage of the receiving circuit 111. An A/D converter 116 is further connected to a subsequent stage of a sample-hold circuit 115. The control unit C has a selection controller C1, which connects a storage unit 113, a display unit 114, and a switching controller SC corresponding to the signal processing circuit 112, the A/D converter 116, and the portable recording medium 105 to each other. The switching controller SC has strength-receiving-antenna number information N1 and image-receiving-antenna number information N2, generates a changeover instruction of the changeover switch SW based on these pieces of number information, and instructs a processing timing of the sample-hold circuit 115, the A/D converter 116, and the selection controller C1. A power supply unit 117 supplies power to respective units, and is achieved by a battery, for example.

The changeover switch SW in the external device 102b selectively switches any one of the receiving antennas A1 to An based on the switching instruction from the switching controller SC, and outputs a radio signal from the switched antenna of the receiving antennas A1 to An to the receiving circuit 111.

The receiving circuit 111 outputs an image signal S1 obtained by amplifying and demodulating the radio signal to the signal processing circuit 112, and outputs a received strength signal S2, which is a received electric-field strength of the amplified radio signal, to the sample-hold circuit 115. The image data processed by the signal processing circuit 112 is stored in the storage unit 113 by the control unit C, and displayed by the display unit 114. The signal sample-held by the sample-hold circuit 115 is converted to a digital signal by the A/D converter 116, and fetched by the control unit C. The selection controller C1 in the control unit C selects a receiving antenna, which has received the largest received electric-field strength of the electric-field strength received during a part of the synchronization period and a horizontal blanking period in the image signal period as a receiving antenna in the image signal period. Further, the selection controller C1 sequentially selects a receiving antenna other than the selected receiving antenna as the receiving antenna during a part of the synchronization period and the horizontal blanking period in the image signal period, and outputs a signal S4, in which the respective receiving antenna numbers are designated as strength-receiving-antenna number information N1 and image-receiving-antenna number information N2, to the switching controller SC. The control unit C stores the received electric-field strength during a part of the synchronization period and the horizontal blanking period in the image signal period and the received electric-field strength during an image receiving period excluding at least the horizontal blanking period in the storage unit 113 in correspondence with the receiving antenna selected at that time, together with the image data. The stored received electric-field strength of respective receiving antennas becomes information for calculating the position of the capsule endoscope 103 in the subject when the image data is received.

The switching controller SC holds the strength-receiving-antenna number information N1 and the image-receiving-antenna number information N2 instructed by the selection controller C1, and instructs the changeover switch SW so as to selectively connect any one of the receiving antennas A1 to An corresponding to the strength-receiving-antenna number information N1 during a part of the synchronization period and the horizontal blanking period in the image signal period. Further, the switching controller SC outputs a signal S5 instructing the changeover switch SW so as to selectively connect any one of the receiving antennas A1 to An corresponding to the image-receiving-antenna number information N2 during the image receiving period excluding at least the horizontal blanking period, to the changeover switch SW, and outputs a signal S3a instructing a sample-hold timing by the sample-hold circuit 115, a signal S3b instructing an A/D conversion timing by the A/D converter 116, and a signal S3c instructing a selection control by the selection controller C1.

Figure 8:
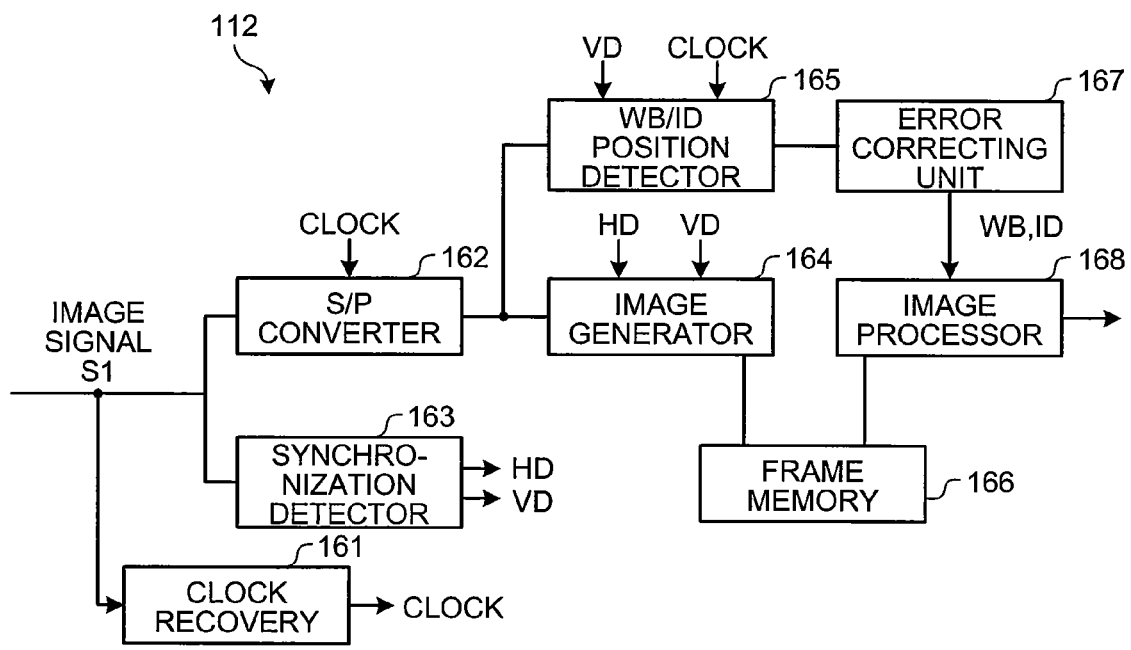
FIG. 8 is a block diagram schematically showing a configuration of a signal processing circuit according to the second embodiment.

The signal processing circuit 112 is explained with reference to FIG. 8. The signal processing circuit 112 has a function for performing predetermined processing with respect to the body cavity image data wirelessly transmitted from the capsule endoscope 103 and received, and storing the body cavity image data in the storage unit 113 (the portable recording medium 105) after subjecting the image data to compression processing and the like. FIG. 8 is a block diagram schematically showing a configuration of the signal processing circuit 112.

As shown in FIG. 8, the signal processing circuit 112 includes the clock recovery 161 to which the image signal from the receiving apparatus 11 is input, an S/P converter 162, a synchronization detector 163, an image generator 164 connected to the output side of the S/P converter 162, a WB/ID position detector 165, a frame memory 166 connected to the output side of the image generator 164, an error correcting unit 167 connected to the output side of the WB/ID position detector 165, and an image processor 168 connected to the frame memory 166 and the error correcting unit 167 to output a processing result to the control unit C.

The clock recovery 161 includes a PLL circuit and the like, reproduces the clock based on the image signal S1, and outputs the clock to the WB/ID position detector 165 and the like. The S/P converter 162 converts the base-band image signal S1 input as a serial signal to a parallel signal, synchronized with the clock. The synchronization detector 163 monitors the data of the input image signal S1, and outputs a pulse of the vertical synchronization signal VD to the image generator 164 and the WB/ID position detector 165, upon detection of, for example, the code "55 00 FF 55 ". Upon detection of, for example, the code "55 AA FF 55", the synchronization detector 163 outputs a pulse of the horizontal synchronization signal HD to the image generator 164. The image generator 164 generates frame image data by performing the image generation processing with respect to the parallel-converted image signal at a timing synchronized with the vertical synchronization signal VD and the horizontal synchronization signal HD, and temporarily stores the frame image data in the frame memory 166.

On the other hand, the WB/ID position detector 165 monitors the count value HCOUNT of the horizontal synchronization signal based on the vertical synchronization signal VD, detects whether the count value HCOUNT has reached the count values HCOUNT "357" and "358" as the positions where the white balance factor data "WB" and the ID information "ID" specific to the capsule are arranged, and when the count values have reached the count values HCOUNT "357" and "358", receives 4-byte data including the Reed-Solomon codes "RS1" and "RS2" immediately thereafter. The error correcting unit 167 performs error correction with respect to the white balance factor data "WB" and the ID information "ID" specific to the capsule by the Reed-Solomon codes "RS1" and "RS2" by using the received 4-byte data, to output the error-corrected right white balance factor data "WB" and ID information "ID" specific to the capsule to the image processor 168. In other words, in the second embodiment, after having detected the code "55 00 FF 55 " indicating the vertical synchronization signal VD, the WB/ID position detector 165 counts the horizontal synchronization signal HCOUNT, specifies the positions of white balance factor data "WB" and the ID information "ID" specific to the capsule, and performs error correction by the Reed-Solomon codes "RS1" and "RS2" added immediately thereafter.

The image processor 168 uses the error-corrected white balance factor data "WB" to perform white balance processing and required image processing such as compression processing, with respect to the frame image data generated and temporarily stored in the frame memory 166, and stores the data in the storage unit 113 (the portable recording medium 105) under control of the control unit C. At the time of such image processing, the image processor 168 checks the error-corrected ID information "ID" specific to the capsule, and when the ID information "ID" does not agree with the ID information "ID" specific to the capsule in the previous frame, determines that the image data is transmitted from another capsule endoscope 103, so that the image data is not stored in the storage unit 113 (the portable recording medium 105).

Thus, in the second embodiment, the Reed-Solomon codes "RS1" and "RS2" are added to the white balance factor information "WB" specific to the capsule endoscope 103 and the ID information "ID" specific to the capsule for deciding the capsule endoscope 103 and transmitted. On the receiving apparatus 102 side, the Reed-Solomon codes "RS1" and "RS2" are used to perform error correction of the white balance factor information "WB" and the ID information "ID" specific to the capsule. Accordingly, even if a bit error such as data garbling occurs in the white balance factor information "WB" and the ID information "ID" specific to the capsule, the information can be corrected to right data by the error correction processing. Particularly, according to the Reed-Solomon codes, data garbling of one byte can be also corrected, which has higher reliability than the Hamming code for correcting one bit. Therefore, tolerance against a bit error in the parameter information such as the white balance factor information "WB" can be increased, and the number of invalidated image signals can be reduced as much as possible in a unit of frame. Further, since the error-correcting codes are added only to the important parameter information such as the white balance factor information "WB" and the ID information "ID" specific to the capsule, and are not added to the image signal itself, which is a greater part of data, redundancy of data can be reduced to the necessity minimum.

Third Embodiment

In the transfer operation of the radio signal between the capsule endoscope 103 and the receiving apparatus 102, synchronization cannot be achieved correctly, if there is one bit error relating to the code "55 00 FF 55 " indicating the vertical synchronization signal VD or the code "55 AA FF 55" indicating the horizontal synchronization signal HD, of 16-bit configuration respectively. Specifically, the code "55 00 FF 55 " indicating the vertical synchronization signal VD has a particular relation with the arrangement position of the white balance factor information "WB" and the ID information "ID" specific to the capsule. Therefore, when the vertical synchronization signal VD cannot be correctly detected, the arrangement position of the white balance factor data "WB", the ID information "ID" specific to the capsule cannot be detected correctly. Further, if the code "55 AA FF 55" indicating the horizontal synchronization signal HD cannot be detected due to a bit error, the line synchronization of the image signal cannot be achieved reliably.

In the third embodiment, therefore, the error-correcting code is added only to the important parameter information such as the white balance factor information "WB" and the ID information "ID" specific to the capsule. However, in the third embodiment, the error-correcting code is also added to the code "55 00 FF 55 " indicating the vertical synchronization signal VD and the code "55 AA FF 55" indicating the horizontal synchronization signal HD.

The parameter/error-correcting code adder 122a in the third embodiment adds Reed-Solomon codes "RS3", "RS4", "RS5", and "RS6" one bit each as the error-correcting code stored beforehand in the parameter memory 128 immediately after the code "55 00 FF 55 " indicating the vertical synchronization signal VD and the code "55 AA FF 55" indicating the horizontal synchronization signal HD transmitted in a specified predetermined arrangement relation.

Figure 11:
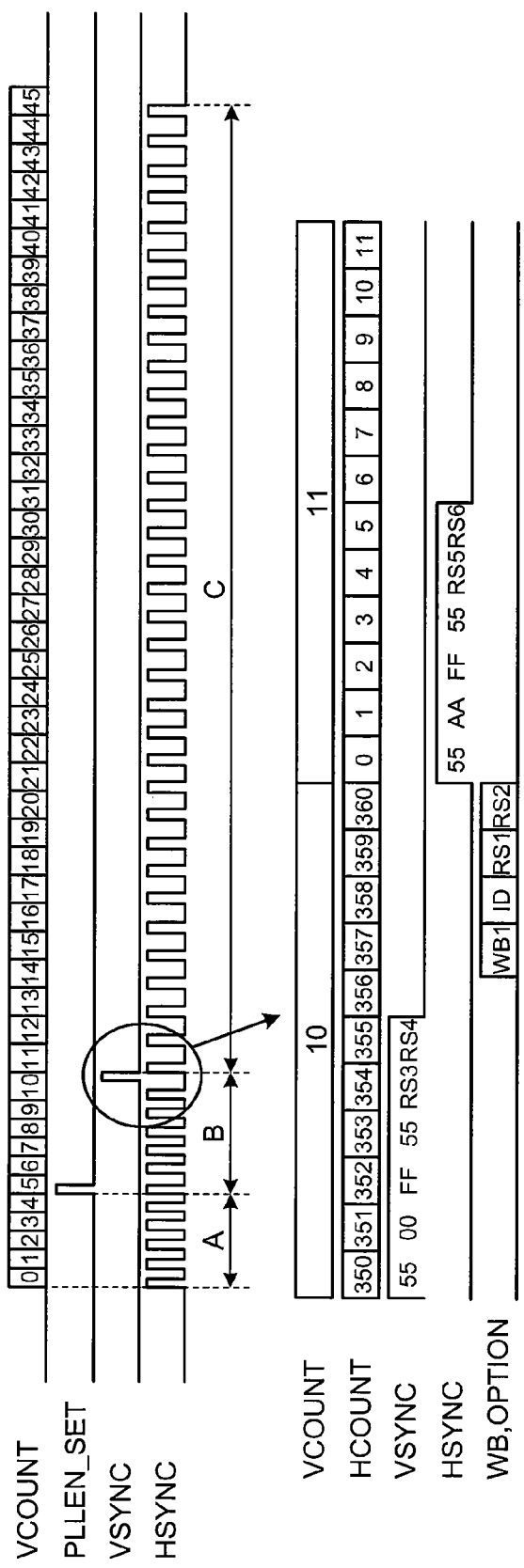
FIG. 11 is a timing chart of a receiving operation of the receiving apparatus according to the third embodiment.

With reference to FIG. 11, which shows a timing chart of a receiving operation of the receiving apparatus 102 in the third embodiment, the 16-bit code of "55 00 FF 55" is used as the code indicating the vertical synchronization signal VSYNC (VD), and the vertical synchronization signal VSYNC (VD) is set so as to be allocated to particular line positions specified by "350", "351", "352", and "353" as count values HCOUNT of the horizontal synchronization signal in the phase having the count value VCOUNT of "10" since start of the operation, and transmitted, and the Reed-Solomon codes "RS3", and "RS4" for error correction are set so as to be allocated to particular line positions specified by "354" and "355" as count values HCOUNT immediately thereafter, and transmitted.

Further, the 16-bit code of "55 AA FF 55" is used as the code indicating the horizontal synchronization signal HSYNC (HV), and the horizontal synchronization signal HSYNC (HV) is set so as to be allocated to particular line positions specified by "0", "1", "2", and "3" as count values HCOUNT of the horizontal synchronization signal in the phase having the count value VCOUNT of "11" since start of the operation, and transmitted, and the Reed-Solomon codes "RS5", and "RS6" for error correction are set so as to be allocated to particular line positions specified by "4" and "5" as count values HCOUNT immediately thereafter, and transmitted.

Figure 10:
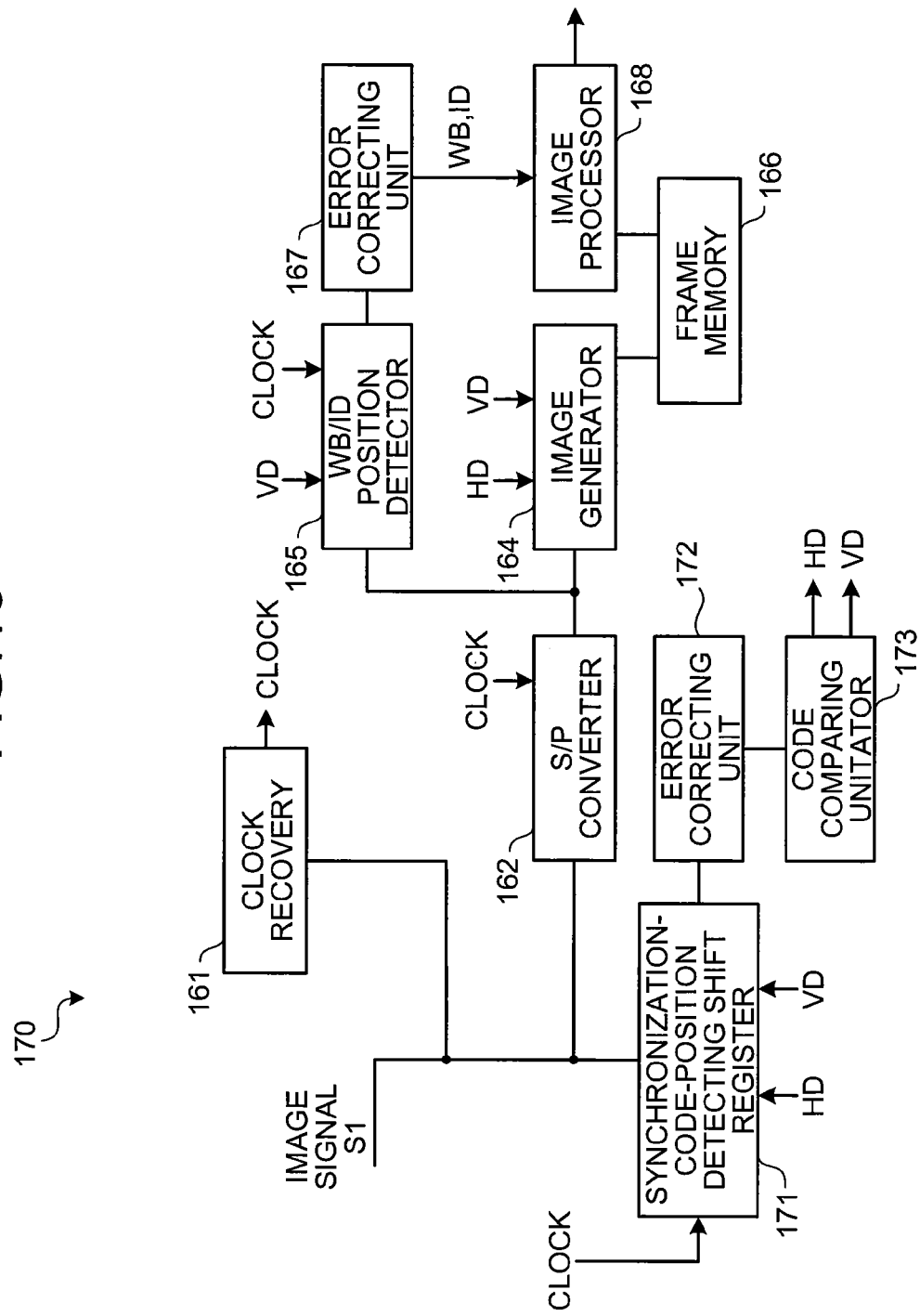
FIG. 10 is a block diagram schematically showing a configuration of a signal processing circuit according to a third embodiment.

A signal processing circuit 170 in the third embodiment is explained with reference to FIG. 10. FIG. 10 is a block diagram schematically showing a configuration of the signal processing circuit 170. The signal processing circuit 170 includes a synchronization-code-position detecting shift register 171, an error correcting unit 172, and a code comparator 173, in addition to the configuration of the signal processing circuit 112.

The synchronization-code-position detecting shift register 171 detects whether the count values VCOUNT and HCOUNT have reached the count value VCOUNT "10" and the count values HCOUNT "350" to "353" where the code indicating the vertical synchronization signal VD should be present, while shifting the image signal S1 input corresponding to the clock, and when the count values have reached these positions, receives 6-byte data including the Reed-Solomon codes "RS3" and "RS4" immediately thereafter. The error correcting unit 172 performs error correction with respect to a code indicating the vertical synchronization signal VD by the Reed-Solomon codes "RS3" and "RS4" by using the received 6-byte data. The code comparator 173 compares and determines whether the error-corrected code indicating the vertical synchronization signal VD agrees with the code "55 00 FF 55" indicating the original vertical synchronization signal VD. When these codes agrees with each other, the code comparator 173 determines that the code has been detected correctly and outputs a pulse of the vertical synchronization signal VD to the image generator 164 and the WB/ID position detector 165. Accordingly, even if there is a bit error in the code indicating the vertical synchronization signal VD, the correct vertical synchronization signal VD can be detected, and the arrangement position of the white balance factor information "WB" and the ID information "ID" specific to the capsule can be correctly detected. The code comparator 73 also outputs the vertical synchronization signal VD to the synchronization-code-position detecting shift register 171, and resets the counter.

Further, the synchronization-code-position detecting shift register 171 detects whether the count values VCOUNT and HCOUNT have reached the count value VCOUNT "11" and the count values HCOUNT "0" to "3" where the code indicating the horizontal synchronization signal HD should be present, while shifting the image signal S1 input corresponding to the clock, and when the count values have reached these positions, receives 6-byte data including the Reed-Solomon codes "RS5" and "RS8" immediately thereafter. The error correcting unit 172 performs error correction with respect to a code indicating the horizontal synchronization signal HD by the Reed-Solomon codes "RS5" and "RS6" by using the received 6-byte data. The code comparator 173 compares and determines whether the error-corrected code indicating the horizontal synchronization signal VD agrees with the code "55 AA FF 55" indicating the original horizontal synchronization signal HD. When these codes agree with each other, the code comparator 173 determines that the code has been detected correctly and outputs a pulse of the horizontal synchronization signal HD to the image generator 164. Accordingly, even if there is a bit error in the code indicating the horizontal synchronization signal HD, the correct horizontal synchronization signal HD can be detected, and the line synchronization can be achieved reliably. The code comparator 173 also outputs the horizontal synchronization signal HD to the synchronization-code-position detecting shift register 171, and resets the counter.

The first to the third embodiments described in this specification can be embodied by combining each other.

INDUSTRIAL APPLICABILITY

The receiving apparatus according to the present invention is useful at the time of receiving a radio signal transmitted from the body-insertable apparatus such as the capsule endoscope and recording the radio signal on a portable recording medium detachably attached thereto. Particularly, the receiving apparatus is suitable for preventing erroneous operations when the portable recording medium can be ejected even during the examination.

The invention claimed is:

1. A receiving apparatus for receiving a radio signal through an antenna, the radio signal being transmitted by a moving transmitting apparatus and having a frame configuration, the frame configuration including at least a main information portion that includes information main part based on an image signal and an added portion that includes synchronization information and parameter information specific to the transmitting apparatus, the receiving apparatus comprising:
  a detecting unit that is configured to detect, from the received radio signal, an arrangement position of the parameter information in a frame configuration in which an error-correcting code is added immediately after the parameter information to be transmitted in a predetermined arrangement position of the frame configuration;
  a parameter information error correcting unit that is configured to perform error correction on the parameter information with the error-correcting code that is added immediately after the detected arrangement position of the parameter information; and
  an image processing unit that is configured to perform image processing on the image signal of the main information portion using the corrected parameter information.

2. The receiving apparatus according to claim 1, further comprising:
  a vertical synchronization code position detecting unit that is configured to detect, from the received radio signal, an arrangement position of a code indicating a vertical synchronization signal to be transmitted in a specified predetermined arrangement relation between the parameter information and the code indicating the vertical synchronization signal in a frame configuration in which an error-correcting code is added immediately after the code indicating the vertical synchronization signal; and
  a vertical synchronization error correcting unit that is configured to perform error correction on the code of the vertical synchronization signal with the error-correcting code that is added immediately after the detected arrangement position of the code indicating the vertical synchronization signal.

3. The receiving apparatus according to claim 1, further comprising:
  a horizontal synchronization code position detecting unit that is configured to detect, from the received radio signal, an arrangement position of a code indicating a horizontal synchronization signal in a frame configuration in which an error-correcting code is added immediately after the code indicating the horizontal synchronization signal to be transmitted in a predetermined arrangement position of the frame configuration; and
  a horizontal synchronization error correcting unit that is configured to perform error correction on the code indicating the horizontal synchronization signal with the error-correcting code that is added immediately after the detected arrangement position of the code indicating the horizontal synchronization signal.

4. The receiving apparatus according to claim 1, wherein the parameter information includes specific ID information for identifying the transmitting apparatus.

5. The receiving apparatus according to claim 1, wherein the parameter information includes white balance factor data used for a white balance process that is performed on imaging data generated by an imaging device for obtaining the image signal in the transmitting apparatus.

6. The receiving apparatus according to claim 1, wherein the parameter information includes data indicating an address of a pixel defect of an imaging device for obtaining the image signal in the transmitting apparatus.

7. The receiving apparatus according to claim 1, wherein the error correcting code is a Reed-Solomon code.

8. A transmitting apparatus for transmitting a radio signal having a frame configuration to be received by a receiving apparatus with an antenna, the frame configuration including at least a main information portion that includes an information main part based on an image signal obtained by imaging and an added portion that includes synchronization information and parameter information specific to the transmitting apparatus, the transmitting apparatus comprising:
- a signal processing unit that is configured to add an error-correcting code for the parameter information to be transmitted in a predetermined arrangement position of the frame configuration immediately after the parameter information.

9. The transmitting apparatus according to claim 8, wherein
- the signal processing unit adds an error-correcting code for a code indicating a vertical synchronization signal to be transmitted in a specified predetermined arrangement relation between the parameter information and the code indicating the vertical synchronization signal in a frame configuration, immediately after the code indicating the vertical synchronization signal.

10. The transmitting apparatus according to claim 8, wherein
- the signal processing unit is configured to add an error-correcting code for a code indicating a horizontal synchronization signal to be transmitted in a predetermined arrangement position of a frame configuration, immediately after the code indicating the horizontal synchronization signal.

11. A transmitting and receiving system comprising:
- a transmitting apparatus that transmits a radio signal having a frame configuration to be received by a receiving apparatus with an antenna, the frame configuration including at least a main information portion that includes an information main part based on an image signal obtained by imaging and an added portion that includes synchronization information and parameter information specific to the transmitting apparatus; and
- a receiving apparatus that is configured to receive the radio signal transmitted by the transmitting apparatus through an antenna, wherein
- the transmitting apparatus includes a signal processing unit that is configured to add an error-correcting code for the parameter information to be transmitted in a predetermined arrangement position of the frame configuration immediately after the parameter information, and
- the receiving apparatus includes
- a detecting unit that is configured to detect, from the received radio signal, an arrangement position of the parameter information in the frame configuration;
- a parameter information error correcting unit that is configured to perform error correction on the parameter information with the error-correcting code that is added immediately after the detected arrangement position of the parameter information; and
- an image processing unit that is configured to perform image processing on the image signal of the main information portion using the corrected parameter information.

\* \* \* \* \*